(12) United States Patent
Kosaka et al.

(10) Patent No.: US 12,419,565 B2
(45) Date of Patent: Sep. 23, 2025

(54) INFORMATION PROCESSING METHOD

(71) Applicant: NEC Corporation, Tokyo (JP)

(72) Inventors: Yuki Kosaka, Tokyo (JP); Masahiro Kubo, Tokyo (JP); Toshinori Hosoi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 585 days.

(21) Appl. No.: 17/763,777

(22) PCT Filed: Oct. 17, 2019

(86) PCT No.: PCT/JP2019/040832
§ 371 (c)(1),
(2) Date: Mar. 25, 2022

(87) PCT Pub. No.: WO2021/075017
PCT Pub. Date: Apr. 22, 2021

(65) Prior Publication Data
US 2022/0330880 A1    Oct. 20, 2022

(51) Int. Cl.
*A61B 5/00*       (2006.01)
*G06N 20/00*    (2019.01)

(52) U.S. Cl.
CPC .......... *A61B 5/4088* (2013.01); *A61B 5/7275* (2013.01); *G06N 20/00* (2019.01)

(58) Field of Classification Search
CPC ..... A61B 5/4088; A61B 5/7275; G06N 20/00
See application file for complete search history.

(56) References Cited

U.S. PATENT DOCUMENTS

2018/0254958 A1* 9/2018 Cheng .................. H04L 41/147
2018/0315182 A1* 11/2018 Rapaka ................. G06T 7/0012
(Continued)

FOREIGN PATENT DOCUMENTS

| CN | 106021377 A | * 10/2016 |
| JP | 2002-157414 A | 5/2002 |
| JP | 2009-244916 A | 10/2009 |
| JP | 2015-159935 A | 9/2015 |
| JP | 2017-027476 A | 2/2017 |
| JP | 2019-160228 A | 9/2019 |

OTHER PUBLICATIONS

S. M. Mostafavi, J. I. Glasgow, S. P. Dukelow, S. H. Scott and P. Mousavi, "Prediction of stroke-related diagnostic and prognostic measures using robot-based evaluation," 2013 IEEE 13th Intl Conf on Rehabilitation Robotics, pp. 1-6, doi: 10.1109/ICORR.2013, pp. 1-6, doi: 10.1109/ICORR.2013.6650457 (Year: 2013).*

(Continued)

*Primary Examiner* — Sun M Li
(74) *Attorney, Agent, or Firm* — Sughrue Mion, PLLC

(57) ABSTRACT

An information processing apparatus according to the present invention includes: a calculating unit configured to calculate, based on subject information including a first assessment value representing an assessment of a subject at a predetermined moment for each of a plurality of items set in FIM (Functional Independence Measure), a prediction value representing an assessment of the subject predicted after the predetermined moment; and a control unit configured to set the prediction value as a provisional assessment value representing a provisional assessment of the subject for a predetermined item of the FIM, and control to output so as to display in a correctable manner on an information processing device operated by an assessor.

9 Claims, 10 Drawing Sheets

(56) References Cited

U.S. PATENT DOCUMENTS

| | | | | |
|---|---|---|---|---|
| 2019/0139631 A1* | 5/2019 | Eshelman | ............... | G16H 20/00 |
| 2020/0176117 A1* | 6/2020 | Lee | ..................... | G06F 18/241 |
| 2020/0237291 A1* | 7/2020 | Sundaram | ............ | A61B 5/4528 |
| 2020/0265950 A1* | 8/2020 | Hosoi | ................... | A61B 5/7264 |
| 2020/0411194 A1* | 12/2020 | Otsuki | ................... | A61H 1/024 |
| 2021/0217509 A1* | 7/2021 | Sato | ..................... | G16H 50/20 |
| 2021/0383921 A1* | 12/2021 | Isobe | .................... | G16H 20/00 |
| 2022/0230096 A1* | 7/2022 | Takamatsu | .............. | G06F 18/24 |

OTHER PUBLICATIONS

T. Prasertsakul, P. Kaimuk and W. Charoensuk, "Defining the rehabilitation treatment programs for stroke patients by applying Neural Network and Decision Trees models," The 7th 2014 Biomedical Engineering International Conference, Fukuoka, Japan, 2014, pp. 1-5, doi: 10.1109/BMEICON.2014.7017422. (Year: 2014).*

G. Sprint, D. J. Cook, D. L. Weeks and V. Borisov, "Predicting Functional Independence Measure Scores During Rehabilitation With Wearable Inertial Sensors," in IEEE Access, vol. 3, pp. 1350-1366, 2015, doi: 10.1109/ACCESS.2015.2468213. (Year: 2015).*

Y. .-J. Chang, H. .-H. Liu and T. .-Y. Wang, "Mobile social networks as quality of life technology for people with severe mental illness," in IEEE Wireless Communications, vol. 16, No. 3, pp. 34-40, Jun. 2009, doi: 10.1109/MWC.2009.5109462. (Year: 2019).*

S. Jecan, L. Rusu, R. Arba and D. Mican, "Mobile application for elders with cognitive impairments," 2017 Internet Technologies and Applications (ITA), Wrexham, UK, 2017, pp. 155-160, doi: 10.1109/ITECHA.2017.8101928. (Year: 2017).*

International Search Report for PCT Application No. PCT/JP2019/040632, mailed on Jan. 7, 2020.

* cited by examiner

Fig.1

| | | |
|---|---|---|
| L4 | INDEPENDENCE | 7 POINTS — COMPLETE INDEPENDENCE |
| | | 6 POINTS — MODIFIED INDEPENDENCE |
| L3 | PARTIAL ASSISTANCE | 5 POINTS — SUPERVISION |
| | | 4 POINTS — MINIMAL ASSISTANCE |
| L2 | ASSISTANCE | 3 POINTS — MODERATE ASSISTANCE |
| | | 2 POINTS — MAXIMAL ASSISTANCE |
| L1 | COMPLETE ASSISTANCE | 1 POINTS — TOTAL ASSISTANCE |

| | | | | |
|---|---|---|---|---|
| COGNITION ITEMS | SOCIAL COGNITION | MEMORY | TOTAL 2 TO 3 POINTS | SUBSECTION ITEMS TOTAL 35 TO 5 POINTS |
| | | PROBLEM SOLVING | | |
| | COMMUNICATION | SOCIAL INTERACTION | TOTAL 15 TO 3 POINTS | |
| | | EXPRESSION (VERBAL/NON-VERBAL) | | |
| | | COMPREHENSION (AUDITORY/VISUAL) | | |
| MOTOR ITEMS | LOCOMOTION | STAIRS | TOTAL 16 TO 3 POINTS | MOTOR ITEMS TOTAL 126 TO 18 POINTS |
| | | WALK/WHEELCHAIR | | |
| | TRANSFER | TUB/SHOWER | TOTAL 91 TO 3 POINTS | |
| | | TOILET | | |
| | | BED/CHAIR/WHEELCHAIR | | |
| | SPHINCTER CONTROL | BOWEL MANAGEMENT | TOTAL 16 TO 3 POINTS | |
| | | BLADDER MANAGEMENT | | |
| | SELF-CARE | TOILETING | TOTAL 42 TO 6 POINTS | |
| | | DRESSING (LOWER BODY) | | |
| | | DRESSING (UPPER BODY) | | |
| | | BATHING | | |
| | | GROOMING | | |
| | | EATING | | |

Fig.4

INFORMATION OF AA AA

[SELF-CARE]

| EATING | GROOMING | BATHING |
|---|---|---|
| 3 | 5 | 2 |

| DRESSING (UPPER BODY) | DRESSING (LOWER BODY) | TOILETING |
|---|---|---|
| 2 | 5 | 2 |

[SPHINCTER CONTROL]

| BLADDER MANAGEMENT | BOWEL MANAGEMENT |
|---|---|
| 5 | 3 |

[TRANSFER]

| BED/WHEELCHAIR | TOILET | TUB/SHOWER |
|---|---|---|
| 2 | 3 | 3 |

[LOCOMOTION]

| WALK/WHEELCHAIR | STAIRS |
|---|---|
| 3 | 3 |

⋮

CONFIRM

Fig.5

INFORMATION OF AA AA

⟨MOTOR FUNCTION ITEMS⟩  FUNCTION TOTAL  POINTS

[SELF-CARE]

| EATING | | GROOMING | | BATHING | | DRESSING (UPPER BODY) | | DRESSING (LOWER BODY) | | TOILETING | |
|---|---|---|---|---|---|---|---|---|---|---|---|
| 5 | V | 5 | V | 3 | V | 5 | V | 6 | V | 7 | V |

[TRANSFER]

| BED/WHEELCHAIR | | TOILET | | TUB/SHOWER | |
|---|---|---|---|---|---|
| 4 | V | 2 | V | 6 | V |

[LOCOMOTION]

| WALK/WHEELCHAIR | | STAIRS | |
|---|---|---|---|
| 5 | V | 7 | V |

[SPHINCTER CONTROL]

| BLADDER MANAGEMENT | | BOWEL MANAGEMENT | |
|---|---|---|---|
| 6 | V | 2 | V |

⟨COGNITION FUNCTION ITEMS⟩  FUNCTION TOTAL  POINTS

[COMMUNICATION]

| COMPREHENSION | | EXPRESSION | |
|---|---|---|---|
| 5 | V | 1 | V |

[SOCIAL COGNITION]

| SOCIAL INTERACTION | | PROBLEM SOLVING | | MEMORY | |
|---|---|---|---|---|---|
| 3 | V | 7 | V | 4 | V |

TOTAL  POINTS

CONFIRM

Fig.6

| INITIAL VALUE | TRUE VALUE | PREDICTION VALUE ||||||
|---|---|---|---|---|---|---|---|
| | | 1 | 2 | 3 | 4 | 5 | 6 | 7 |
| 1 | 1 | | (2)-0 | (2)-1 | (2)-1 | (2)-1 | (2)-2 | (2)-2 |
| | 2 | (1) | | (2)-1 | (2)-1 | (2)-1 | (2)-2 | (2)-2 |
| | 3 | (1) | (1)-1 | | (2)-0 | (2)-0 | (2)-1 | (2)-1 |
| | 4 | (1) | (1)-1 | (1)-0 | | (2)-0 | (2)-1 | (2)-1 |
| | 5 | (1) | (1)-1 | (1)-0 | (1)-0 | | (2)-1 | (2)-1 |
| | 6 | (1) | (1)-2 | (1)-1 | (1)-1 | (1)-1 | | (2)-0 |
| | 7 | (1) | (1)-2 | (1)-1 | (1)-1 | (1)-1 | (1)-0 | |
| 2 | 2 | | | (2)-1 | (2)-1 | (2)-1 | (2)-2 | (2)-2 |
| | 3 | | (1)-1 | | (2)-0 | (2)-0 | (2)-1 | (2)-1 |
| | 4 | | (1)-1 | (1)-0 | | (2)-0 | (2)-1 | (2)-1 |
| | 5 | | (1)-1 | (1)-0 | (1)-0 | | (2)-1 | (2)-1 |
| | 6 | | (1)-2 | (1)-1 | (1)-1 | (1)-1 | | (2)-0 |
| | 7 | | (1)-2 | (1)-1 | (1)-1 | (1)-1 | (1)-0 | |
| 3 | 3 | | | | (2) | (2) | (2) | (2) |
| | 4 | | | (1) | | (2) | (2) | (2) |
| | 5 | | | (1) | (1) | | (2) | (2) |
| | 6 | | | (1) | (1) | (1) | | (2) |
| | 7 | | | (1) | (1) | (1) | (1) | |
| 4 | 4 | | | | | (2) | (2) | (2) |
| | 5 | | | | (1) | | (2) | (2) |
| | 6 | | | | (1) | (1) | | (2) |
| | 7 | | | | (1) | (1) | (1) | |
| 5 | 5 | | | | | | (2) | (2) |
| | 6 | | | | | (1) | | (2) |
| | 7 | | | | | (1) | (1) | |
| 6 | 6 | | | | | | | (2) |
| | 7 | | | | | | (1) | |
| 7 | 7 | | | | | | | |

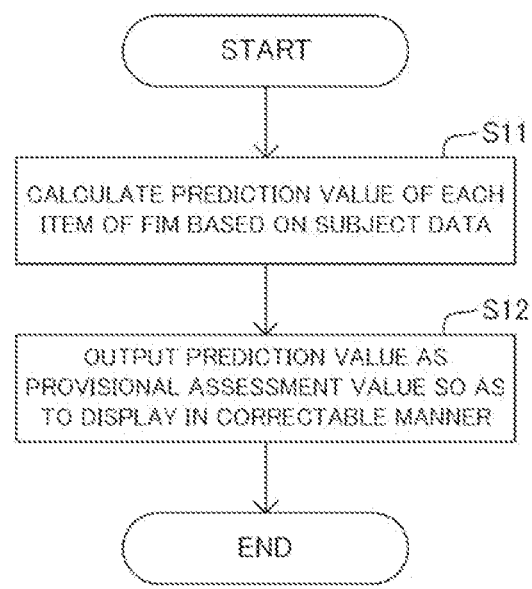

INFORMATION PROCESSING METHOD

This application is a National Stage Entry of PCT/JP2019/040832 filed on Oct. 17, 2019, the contents of all of which are incorporated herein by reference, in their entirety.

TECHNICAL FIELD

The present invention relates to an information processing method, an information processing apparatus, and a program.

BACKGROUND ART

Injuries, illnesses, aging and so on may reduce a function of activities of daily living and a cognition function. In such cases, rehabilitation is performed in a rehabilitation facility for recovery of a function of activities of daily living and a cognition function. A rehabilitation facility needs to grasp the conditions of a motor function related to activities of daily living and a cognition function of a patient subject to rehabilitation and, as an example of an index for measuring such conditions of the patient, the FIM (Functional Independence Measure: an index for measuring a motor function related to activities of daily living and a cognition function) is used. For example, as shown in Patent Document 1, the FIM includes a total of eighteen items including thirteen kinds of motor items and five kinds of cognition items, and each of the items is assessed by four or seven levels of degrees of need for assistance.

In a rehabilitation facility, in order to effectively perform rehabilitation of a patient, a rehabilitation plan is reviewed depending on the situation of the patient. For this, a therapist, who is a person performing rehabilitation of a patient, needs to check the assessment values of the FIM of the patient. For example, a therapist performs an operation of recognizing a difference between the target and the current state of the assessment values of the FIM in rehabilitation of a patient and reviewing the contents of the menu of rehabilitation to be executed in accordance with the difference. Therefore, it is desirable that the assessment values of the FIM are the result of the latest patient's condition assessment at all times. The abovementioned FIM is an example as an index for measuring the condition of a human body of a patient, and it may be possible to assess items set in another index for assessing the condition of a human body different from the FIM and review the contents of the menu of rehabilitation to be executed based on the assessment values.

Patent Document 1: Japanese Unexamined Patent Application Publication No. JP-A 2017-027476

In order to assess each item of the FIM, a therapist needs time for assessment, but there is a case where a therapist cannot spare time for assessment because he/she is in rehabilitation work or a case where a therapist cannot assess just by observing a patient. Besides, since the FIM includes eighteen items, it is difficult to keep the assessment values of the eighteen items of the FIM represent the latest patient's condition at all times. In addition, the FIM represents the degree of motor function and cognition function of a patient and may often show no change even if assessment is performed every day.

Since a therapist is busy and the FIM does not change at all times as described above, it is possible that a therapist does not perform assessment of the FIM. Then, since the FIM does not always represent the latest patient's condition, there may be a case where, even if the therapist recognizes a difference between the target and the current state of the assessment values of the FIM in rehabilitation of a patient and decides a rehabilitation menu in accordance with the difference, the menu is not appropriate for the patient.

SUMMARY

Accordingly, an object of the present invention is to provide an information processing method, an information processing apparatus and a program that can solve the abovementioned problem that the assessment of the FIM is not performed by a therapist.

An information processing method as an aspect of the present invention includes: calculating, based on subject information including a first assessment value representing an assessment of a subject at a predetermined moment for each of a plurality of items set in FIM (Functional Independence Measure), a prediction value representing an assessment of the subject predicted after the predetermined moment; and setting the prediction value as a provisional assessment value representing a provisional assessment of the subject for a predetermined item of the FIM, and outputting so as to display in a correctable manner on an information processing device operated by an assessor.

Further, an information processing apparatus as an aspect of the present invention includes: a calculating unit configured to calculate, based on subject information including a first assessment value representing an assessment of a subject at a predetermined moment for each of a plurality of items set in FIM (Functional Independence Measure), a prediction value representing an assessment of the subject predicted after the predetermined moment; and a control unit configured to set the prediction value as a provisional assessment value representing a provisional assessment of the subject for a predetermined item of the FIM, and control to output so as to display in a correctable manner on an information processing device operated by an assessor.

Further, a computer program as an aspect of the present invention includes instructions for causing an information processing apparatus to realize: a calculating unit configured to calculate, based on subject information including a first assessment value representing an assessment of a subject at a predetermined moment for each of a plurality of items set in FIM (Functional Independence Measure), a prediction value representing an assessment of the subject predicted after the predetermined moment; and a control unit configured to set the prediction value as a provisional assessment value representing a provisional assessment of the subject for a predetermined item of the FIM, and control to output so as to display in a correctable manner on an information processing device operated by an assessor.

With the configurations as described above, the present invention can prompt an assessor to execute the assessment of the FIM.

BRIEF DESCRIPTION OF DRAWINGS

FIG. 1 is a view for describing the FIM;

FIG. 4 is a view showing an example of a display screen displayed on an information processing device disclosed in FIG. 1;

FIG. 5 is a view showing an example of a display screen displayed on the data management apparatus disclosed in FIG. 1;

FIG. 6 is a view showing a standard for setting the number of learning data based on a prediction value and an actual assessment value of the FIM of a patient;

FIG. 10 is a flowchart showing an operation of the information processing apparatus in the second example embodiment of the present invention.

EXAMPLE EMBODIMENTS

First Example Embodiment

Figure 7:
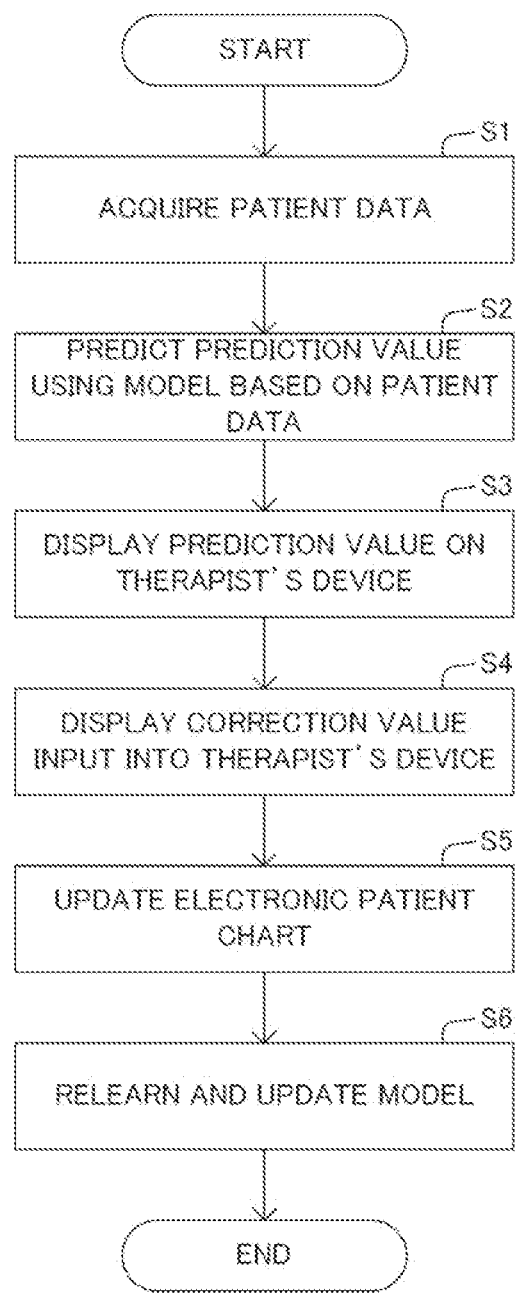
FIG. 7 is a flowchart showing an operation of the information processing system disclosed in FIG. 1.

A first example embodiment of the present invention will be described with reference to FIGS. 1 to 7. FIGS. 1 to 6 are views for describing a configuration of an information processing system, and FIG. 7 is a view for describing a processing operation of the information processing system.
[Configuration]

An information processing system according to the present invention is used for, in a case where a patient (a subject) whose function of activities of daily living and cognition function have deteriorated due to injury, illness, aging or the like is rehabilitated in a rehabilitation facility for recovery of the function of activities of daily living and the cognition function, recording the condition of the patient. Specifically, the information processing system is used for, by using the FIM (Functional Independence Measure) that is an index for measuring a motor function related to activities of daily living and a cognition function of a patient, recording the assessment value of each item of the FIM assessed at any timing. By thus recording the assessment value of each item of the FIM of the patient, the facility can efficiently rehabilitate the patient.

Here, the FIM that is an index for measuring a motor function related to activities of daily living and a cognition function of a patient will be described with reference to FIG. 1. As shown in FIG. 1, the FIM includes a total of eighteen items including thirteen kinds of motor items for assessing the "motor function" of a patient and five kinds of cognition items for assessing the "cognition function" of a patient. Specifically, the FIM includes, as the abovementioned motor items, items for assessing the patient's function of activities of a "self-care" category such as "eating", "grooming", "bathing", "dressing (upper body)", "dressing (lower body)" and "toileting", items for assessing the patient's function of activities of a "sphincter control" category such as "bladder management" and "bowel management", items for assessing the patient's function of activities of a "transfer" category such as "bed/chair/wheelchair", "toilet" and "tub/shower", and items for assessing the patient's function of activities of a "locomotion" category such as "walk/wheelchair" and "stairs". Moreover, the FIM includes, as the abovementioned cognition items, items for assessing the patient's function of a "communication" category such as "comprehension (auditory/visual)" and "expression (verbal/non-verbal), and items for assessing the patient's function of a "social cognition" category such as "social interaction", "problem solving" and "memory".

With the FIM, each of the abovementioned items is assessed by four or seven levels of degrees of assistance necessary for a patient. For example, as shown in the upper right part of FIG. 1, each item may be assessed by four levels of degrees including "L1: complete dependence on helper", "L2: helper", "L3: partial dependence on helper", and "L4: no helper". Moreover, for example, each item may be assessed by seven levels of degrees using scores including "one point: total assistance", "two points: maximal assistance", "three points: moderate assistance", "four points: minimal assistance, "five points: supervision", "six points: modified independence", and "seven points: complete independence". In the case of the assessment by seven levels using scores, a patient may be assessed by aggregating scores for each item, each category, and each function.

In general, the assessment of each item of the FIM described above is performed majorly by a therapist (assessor) who is a specialist performing rehabilitation of a patient. A therapist is, for example, an "occupational therapist (OP)", a "physical therapist (PT)", or a "speech-hearing therapist (ST)". However, a therapist is not limited to the abovementioned persons.

The assessment value of each item of the FIM described above is input into a data management apparatus 10 by the abovementioned therapist and stored as patient data (subject information). For example, the data management apparatus 10 stores patient data of each patient as an electronic patient chart. In an electronic patient chart, information such as "gender", "age group", "consciousness level (JCS: Japan Coma Scale)", "disease name" "paralysis condition" "assessment values of each item of FIM at respective moments such as at admission and after execution of rehabilitation (first assessment value, second assessment value)" and "rehabilitation execution history (execution date, execution time, menu, and so on)" are stored as patient data, for example. However, patient data is not necessarily limited to including the information of the contents mentioned above, and may include only part of the abovementioned information, or may include other information.

According to the present invention, the data management apparatus 10 is configured in a manner as stated below so as to predict the assessment value of each item of the FIM of a patient at any timing, for example, once a day by using the patient data, and also realize prompting a therapist to input an actual assessment value to the prediction.

Figure 2:
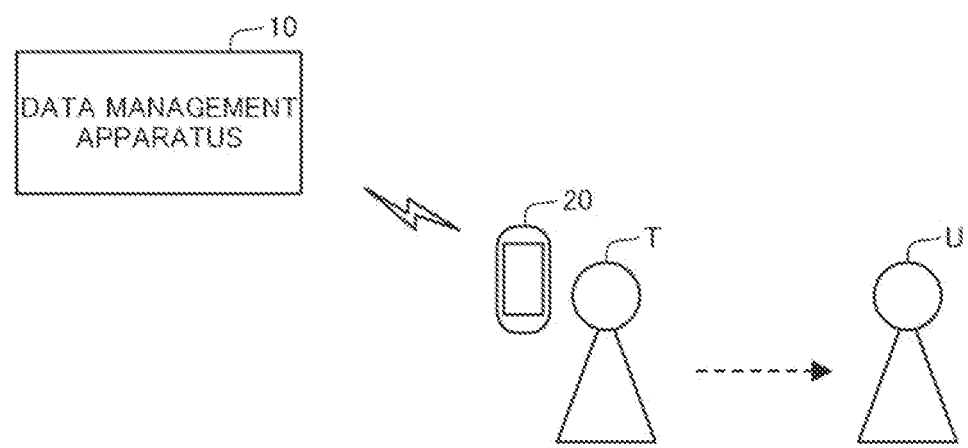
FIG. 2 is a view showing an entire configuration of an information processing system according to the present invention.

The data management apparatus 10 includes one or a plurality of information processing apparatuses each including an arithmetic logic unit and a storage unit. To the data management apparatus 10, an information processing device 20 operated by a therapist T who rehabilitates a patient U is connected via wireless communication as shown in FIG. 2. The information processing device 20 may be configured by any information processing device such as a tablet device or smartphone provided with a touchscreen display or a personal computer placed on a predetermined desk. A tablet device or a smartphone serving as the information processing device 20 may be one that is brought and carried by a therapist on the job, for example, during rehabilitation.

Figure 3:
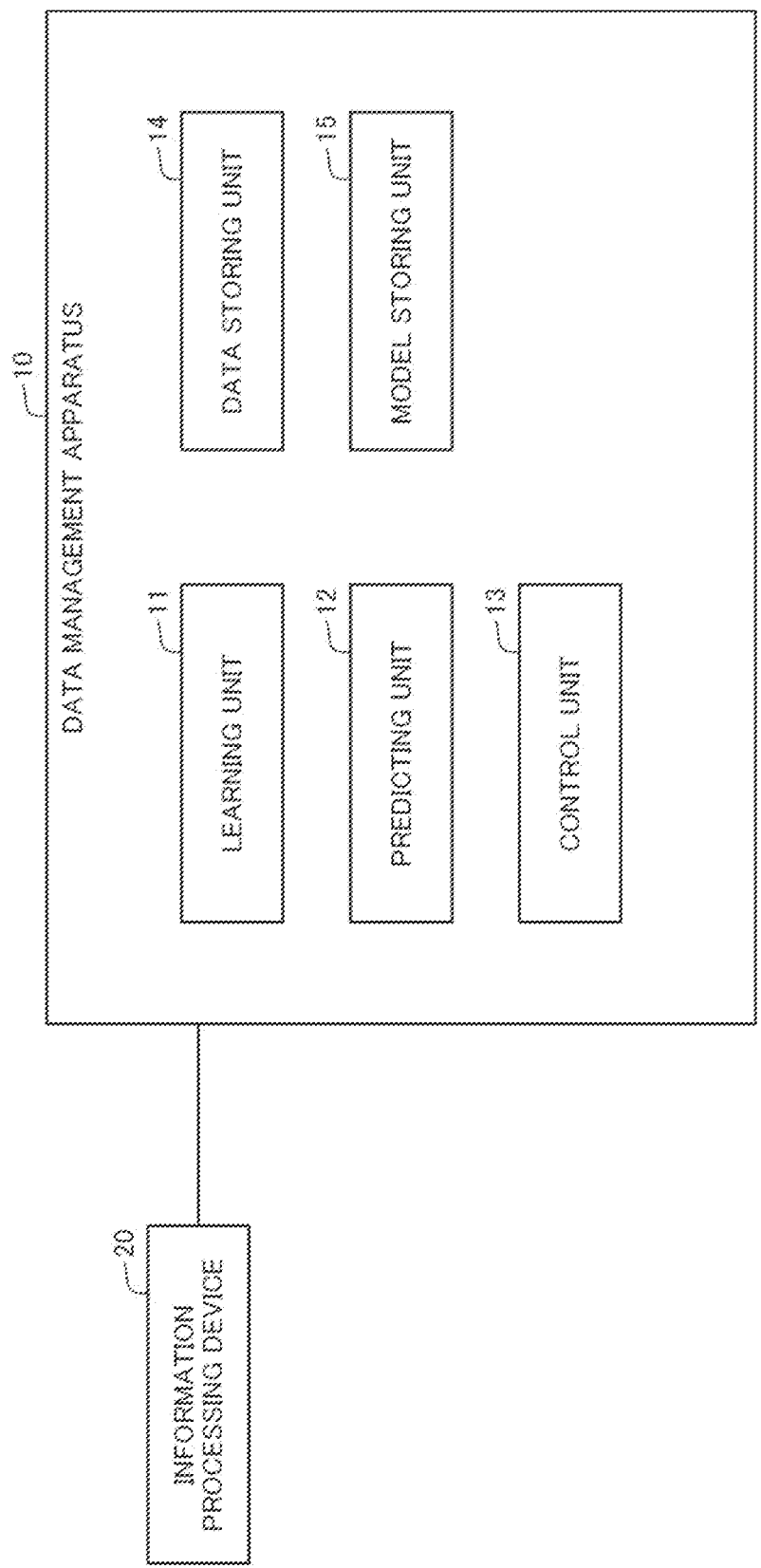
FIG. 3 is a block diagram showing a configuration of a data management apparatus disclosed in FIG. 1.

The data management apparatus 10 includes a learning unit 11, a predicting unit 12, and a control unit 13 that are structured by execution of the program by the arithmetic logic unit as shown in FIG. 3. The data management apparatus 10 also includes a data storing unit 14 and a model storing unit 15 that are formed in the storage unit. The respective components will be described in detail below.

The data storing unit 14 stores an electronic patient chart for each patient U, and stores patient data as described above. That is to say, the data storing unit 14 stores "basic information" such as "gender", "age group", "consciousness level", "disease name" and "paralysis condition" and "rehabilitation information" such as "assessment value of each item of FIM at each moment" and "rehabilitation execution history (execution date, execution time, menu, and so on)" of each patient U. The data storing unit 14 also stores a provisional assessment value that is a prediction value obtained by predicting an assessment of each item of the FIM of a patient as will be described later in a different storage region from the electronic patient chart.

The data storing unit 14 stores therapist information, which is information of each therapist who rehabilitates the patient U. Herein, the therapist information includes, for example, identification information identifying a therapist and attribute information representing the attribute of a therapist. The attribute information of a therapist is, for example, information representing the degree of experience as a therapist and, as one example, includes information representing an attribute of "expert" "competent" or "beginner" in descending order of experience degree. However, the attribute information of a therapist may be information representing any attribute.

The model storing unit 15 stores a model for calculating a prediction value of an assessment value of each item of the FIM from the patient data. The model is generated by machine learning by the learning unit 11 using the patient data stored in the data storing unit 14 as learning data as will be described later. However, the model is not limited to being generated by the learning unit 11, and may be generated by another apparatus and by another method.

The learning unit 11 generates a model for calculating a prediction value of an assessment value of each item of the FIM by performing machine learning using existing patient data as learning data. For example, the learning unit 11 generates, by machine learning, a model where "basic information" such as "gender", "age group", "consciousness level", "disease name" and "paralysis condition" and "rehabilitation information" such as "assessment value of each item of FIM at admission or at a predetermined moment (first assessment value)" and "rehabilitation execution history" included by patient data are input values (explanatory variables) and "actual assessment value of each item of FIM (second assessment value)" is an output value (objective variable). That is to say, the learning unit 11 learns so as to perform prediction using a linear regression model where "rehabilitation information" is an explanatory variable and "actual assessment value of each item of FIM (second assessment value)" of a prediction subject is an objective variable. At this time, the learning unit 11 can determine a parameter of the linear regression model, for example, by applying a known method such as the least-squares method to the existing patient data. Consequently, the generated model is configured to output a prediction value of an assessment value of each item of the FIM with patient data as an input value.

Further, the learning unit 11 also has a function to, every time an actual assessment value (second assessment value) of the patient U is input as will be described later, learn so as to correct the model by using patient data including the actual assessment value as learning data. The function of the learning unit 11 to correct the model will be described later.

The predicting unit 12 calculates a prediction value that is an assessment value of each item of the FIM for a predetermined patient U by using the model stored in the model storing unit 15. For example, the predicting unit 12 inputs "basic information" such as "gender", "age group", "consciousness level" and "paralysis condition" and "rehabilitation information" such as "assessment value of each item of FIM at admission or at predetermined moment (first assessment value)" and "rehabilitation execution history" included by the patient data of the patient U into a model such as a linear regression model where the value of a parameter has been learned as described above, and sets an output value from the model as a prediction value of an assessment value of each item of the FIM. However, the predicting unit 12 is not necessarily limited to calculating a prediction value by using the model as described above, and may calculate a prediction value by another method. In this example embodiment, any machine learning model for solving a prediction problem may be used. For example, support vector regression may be used as a prediction model.

The control unit 13 sets the prediction value predicted by the predicting unit 12 as a provisional assessment value representing a provisional assessment of each item of the FIM, and stores into the data storing unit 14 separately from the electronic patient chart. Then, the control unit 13 outputs the stored provisional assessment value of each item of the FIM of the patient U so as to display on a display of the information processing device 20 operated by the therapist T. At this time, the control unit 13 compares the provisional assessment value of each item of the FIM of the patient with the assessment value stored in the electronic patient chart and, only in a case where there is a difference therebetween, outputs the provisional assessment value so as to display on the information processing device 20. The control unit 13 outputs the provisional assessment value of the patient U so as to display on the information processing device 20 at a timing such as immediately before the scheduled start time to execute rehabilitation on a predetermined patient U by the therapist T, immediately after the scheduled finish time of the rehabilitation, previously determined time when rehabilitation for one day has finished, or a case where the therapist T requests for data of the predetermined patient U via the information processing device 20. As an example, the control unit 13 displays a score that is a provisional value for each item of the FIM on the display of the information processing device 20 as shown in FIG. 4. In the example of FIG. 4, an assessment value of each item of the FIM is represented by a seven-level score, and the control unit 13 displays in a manner that the item "eating" of the category "self-care" is "3 points" and the item "bladder management" of the category "sphincter control" is "5 points", for example.

Further, the control unit 13 outputs to the information processing device 20 so as to display in a manner that the therapist T can correct a provisional assessment value on the information processing device 20. That is to say, the control unit 13 outputs a provisional assessment value so as to display the provisional assessment value on the display screen of the information processing device 20 such as a tablet device or a personal computer. Specifically, when an instruction to correct the displayed provisional assessment value is input from the therapist T, the information processing device 20 corrects the provisional assessment value to a correction value in accordance with the instruction to correct, and notifies the correction value to the control unit 13 of the data management apparatus 10. In response to this, the control unit 13 corrects the provisional assessment value stored in the data storing unit 14 to the correction value. In a case where a provisional assessment value is displayed on the touchscreen display of the information processing device 20 as shown in FIG. 4, the therapist T taps a position displaying the provisional assessment value to display values "1 to 7" in a selectable manner, and the therapist T taps and selects any of the values to input the selected value as a correction value in place of the provisional assessment value.

The control unit 13 may display the abovementioned provisional assessment value of the patient U on the data management apparatus 10 or another information processing apparatus. As an example, the control unit 13 outputs a score that is a provisional assessment value for each item of the FIM so as to display on the display of the data management apparatus 10 in a correctable manner as shown in FIG. 5. Specifically, the control unit 13 displays a pull-down menu of changeable values "1 to 7" in a selectable manner when the therapist T clicks on or around a position displaying a score that is a displayed provisional assessment value. When the therapist T clicks on and select any of the values, the selected value is input as a correction value in place of the provisional assessment value. At this time, the control unit 13 may total the scores that are the displayed provisional assessment values and correction values. For example, the control unit 13 may calculate and display the total value of the scores of the respective functions or the total value of the scores of all the items of the patient U.

Further, when an operation of confirming an assessment value is input from the therapist T into the information processing device 20 or the data management apparatus 10, the control unit 13 confirms a currently displayed assessment value for each item of the FIM as a current actual assessment value (second assessment value) and records as a current assessment value into the electronic patient chart. At this time, with regard to an assessment value of each item of the FIM, in a case where a provisional assessment value is not corrected, the provisional assessment value becomes an actual assessment value, and in a case where an assessment value is corrected to a correction value, the correction value becomes an actual assessment value. The therapist T inputs an operation of confirming an assessment value by pressing a "confirm" button as shown in FIGS. 4 and 5. There is a case where an operation of confirming an assessment value is not performed by the therapist T even at the end of a day (for example, at night such as 20:00) and, in case for such a situation, the control unit 13 may perform the following process. For example, the control unit 13 performs a process of outputting an alert such as an email to a superior (boss, supervisor, or the like) of the therapist T, or outputting an alert before executing the first rehabilitation of the patient U the next day. With this, the control unit 13 prompts the therapist T or his/her boss or the like to confirm an assessment value.

When, for each item of the FIM, a "prediction value" that is a provisional assessment value stored in the data storing unit 14 separately from the electronic patient chart is corrected to a correction value and recorded as an "actual assessment value" into the electronic patient chart, the control unit 13 associates "prediction value", "actual assessment value", and "identification information of therapist who modified" with each other for each item of the FIM, and records as a correction history into the data storing unit 14.

Here, the abovementioned learning unit 11 will be further described. The learning unit 11 further performs machine learning so as to correct the model based on the actual assessment value input in the above manner. Specifically, first, in a case where a provisional assessment value is corrected to a correction value by the therapist T as described above, that is, in a case where there is a difference of a predetermined value or more between the provisional assessment value and the actual assessment value according to the correction history recorded in the data storing unit 14, the learning unit 11 performs relearning of the model by using the patient data as learning data. At this time, in the same manner as described above, the learning unit 11 corrects the model by machine learning by using learning data including a combination where "basic information" such as "gender", "age group", "consciousness level", "disease name" and "paralysis condition" and "rehabilitation information" such as "assessment value of each item of FIM at admission or at predetermined moment (first assessment value)" and "rehabilitation execution history" in the patient data are input values (explanatory variables) and "actual assessment value of each item of FIM (second assessment value)" confirmed after execution of rehabilitation in the above manner is an output value (objective variable).

Further, at the time of relearning of the model described above, the learning unit 11 changes the number of learning data to be used depending on the magnitudes of a prediction value and an actual assessment value that is a correction value obtained by correction recorded as the correction history. At this time, particularly in a case where an actual assessment value is smaller than a prediction value than in a case where an actual assessment value is larger than a prediction value, the learning unit 11 makes the number of learning data including an actual assessment value corrected at the time larger, and corrects the model by using the learning data. For example, in a case where an actual assessment value is larger than a prediction value, that is, in a case where the degree of recovery of a patient is predicted to be lower, the learning unit 11 increases the number of learning data including a corrected actual assessment value $\alpha$ times ($\alpha$: a positive value larger than 1). On the contrary, in a case where an actual assessment value is smaller than a prediction value, that is, in a case where the degree of recovery of a patient is predicted to be higher, the learning unit 11 increases the number of learning data including a corrected actual assessment value $\gamma\alpha$ times ($\gamma$: a positive value larger than 1) to make the number of learning data larger than in a case where the degree of recovery of a patient is predicted to be lower. In this case, the learning unit 11 is not limited to making the number of learning data $\gamma\alpha$ times, but may multiply by a value larger than $\alpha$. This is because if the degree of recovery of a patient is predicted to be higher, rehabilitation necessary for recovery may not be executed based on the actual situation, so that the learning unit 11 performs relearning of the model so as to avoid predicting a prediction value to be higher than an actual assessment value. It is assumed that the abovementioned case of multiplying the number of learning data by $\alpha$ is case (1) and the abovementioned case of multiplying the number of learning data by $\gamma\alpha$ is case (2).

Furthermore, the learning unit 11 further changes the number of learning data increased depending on the magnitudes of a prediction value and an actual assessment value as described above, depending on the magnitude of the difference between the prediction value and the actual assessment value. At this time, as the actual assessment value is larger or smaller with respect to the prediction value, the learning unit 11 further increases the number of learning data in case (1) of multiplying by $\alpha$ or case (2) of multiplying by $\gamma\alpha$ described above. As an example, for each initial value that is an assessment value of the FIM at predetermined time such as before rehabilitation or at admission of a patient, cases (1)-0, (1)-1, (1)-2, (2)-0, (2)-1 and (2)-2 are set for the respective cases (1) and (2) depending on the difference between a prediction value and an actual assessment value (true value) as shown in FIG. 6, and the learning unit 11 increases the number of learning data in the following manner;

(1)-0: further multiply the number of learning data in case (1) by β (β: a positive value larger than 1),
(1)-1: further multiply the number of learning data in case (1) by 2β (β: a positive value larger than 1),
(1)-2: further multiply the number of learning data in case (1) by 3β (β: a positive value larger than 1),
(2)-0: further multiply the number of learning data in case (2) by β (β: a positive value larger than 1),
(2)-1: further multiply the number of learning data in case (2) by 2β (β: a positive value larger than 1), and
(2)-2: further multiply the number of learning data in case (2) by 3β (β: a positive value larger than 1).

The learning unit 11 may further change the number of learning data depending on the attribute of the therapist T having assessed the actual assessment value. For example, it is assumed that, as described above, information representing the degree of experience as a therapist is previously recorded as attribute information of the therapist T and, as an example, an attribute of "expert", "competent" or "beginner" is set in decreasing order of experience degree. It can be said that as the degree of experience of the therapist T is higher, the therapist has a higher degree of reliability. Then, in this case, as the degree of experience is higher, the learning unit 11 increases the number of learning data including the actual assessment value assessed by the therapist and performs correction of the model. For example, the learning unit 11 further changes the number of learning data having been changed as described above by multiplying by 2 in the case of "expert", by 1 in the case of "competent", and by 0.5 in the case of "beginner". That is to say, as the degree of experience of a therapist is higher, the learning unit 11 determines that the therapist has a higher degree of reliability, and corrects the model so that the actual assessment value assessed by the therapist is greatly reflected.

At the time of relearning the model, the learning unit 11 may change the weight of learning data depending on the result of comparison between the prediction value and the actual assessment value or the attribute of the therapist. For example, in the case of increasing the number of learning data as described above, the learning unit 11 may increase the weight of learning data.

[Operation]

Next, an operation of the data management apparatus 10 and the information processing device 20 configuring the information processing system described above will be described with reference to a flowchart of FIG. 7. First, the data management apparatus 10 acquires patient data of a patient U who is scheduled to undergo rehabilitation (step S1). Then, the data management apparatus 10 predicts a prediction value of an assessment value of a case where the patient U undergoes rehabilitation to be executed based on the acquired patient data (step S2). For example, the data management apparatus 10 inputs "basic information" such as "gender", "age group", "consciousness level", "disease name" and "paralysis condition" and "rehabilitation information" such as "assessment value of each item of FIM at admission or at predetermined moment (first assessment value)" and "rehabilitation execution history" included by the patient data of the patient U, into a model previously generated and stored in the model storing unit 15, and sets an output value calculated by the model as a prediction value of an assessment value of each item of the FIM.

The data management apparatus 10 may previously acquire patient data of many patients U as learning data and generate, by machine learning, a model where "basic information" such as "gender", "age group", "consciousness level", "disease name" and "paralysis condition" and "rehabilitation information" such as "assessment value of each item of FIM at admission or at predetermined moment (first assessment value)" and "rehabilitation execution history" are input values (explanatory variables) and "assessment value of each item of FIM actually assessed (second assessment value)" is an output value.

Subsequently, the data management apparatus 10 records the prediction value predicted in the above manner as a provisional assessment value representing a provisional assessment of each item of the FIM of the patient U into the data storing unit 14. Then, the data management apparatus 10 outputs the provisional assessment value of each item of the FIM of the patient U so as to display on the display of the information processing device 20 operated by the therapist T rehabilitating the patient U (step S3). With this, for example, as shown in FIG. 4, a score that is the provisional assessment value is displayed for each item of the FIM of the patient U on the display of the information processing device 20 operated by the therapist T. The data management apparatus 10 may display the provisional assessment value of the patient U on a display device of the data management apparatus 10 as shown in FIG. 5 in accordance with an operation by the therapist T.

After that, the therapist T assesses each item of the FIM of the patient U after rehabilitating the patient U or at any timing. Then, the therapist T checks the score that is the provisional assessment value of each item of the FIM output to the information processing device 20 so as to be displayed and, in a case where the provisional assessment value is different from an actual assessment value, inputs a correction value obtained by correcting the provisional assessment value to the actual assessment value into the information processing device 20. Then, the information processing device 20 outputs so as to display the correction value in place of the provisional assessment value (step S4).

Then, when the therapist T completes the correction of the assessments of the respective items of the FIM displayed on the information processing device 20 and, for example, performs a confirmation process such as pressing the "confirm" button displayed on the information processing device 20, the corrected information is notified from the information processing device 20 to the data management apparatus 10. Upon receiving the notification from the information processing device 20, the data management apparatus 10 confirms the value input as the assessment value of each item of the FIM as an actual assessment value (second assessment value) and records into the electronic patient chart (step S5). At this time, the data management apparatus 10 records the "prediction value" before the correction, the "actual assessment value" after the correction, and "identification information of therapist" who has performed the correction into the data storing unit 14.

After that, the data management apparatus 10 further performs machine learning so as to correct the model by using learning data including the actual assessment value input by the therapist T and recorded as described above (step S6). At this time, the data management apparatus 10 increases the number of learning data depending on the magnitudes of the prediction value and the actual assessment value, or further increases the number of learning data depending on the magnitude of the difference between the prediction value and the actual assessment value. Moreover, the data management apparatus 10 changes the number of learning data depending on an attribute representing experience or the like of the therapist T having performed the assessment of the actual assessment value. Consequently, it is possible to correct the model to a more adequate model. The corrected model is used at the time of calculating a prediction value that is an assessment of each item of the FIM of the patient U later.

A timing for further performing machine learning to correct the model as described above is, for example, after the final update of the assessment value on each day. This is because there may be a plurality of therapists T who rehabilitate the patient U and, in such a case, timings when the respective therapists correct the prediction value, that is, timings when the respective therapists perform an actual assessment are not the same. Therefore, for example, final update time is set for each day, and relearning of the model is performed by using the final update result of the assessment value at a moment beyond the time. However, the timing for relearning the model can be freely selected and may be, for example, after all the therapists T related to the patient U finish inputting or at any timing.

Thus, according to the present invention, a prediction value of an assessment value of each item of the FIM of the patient U is displayed on the information processing device 20 or the data management apparatus 10 operated by the therapist T so that the prediction value can be corrected. By thus inputting the prediction value of the FIM in advance, the therapist T can be motivated to confirm and correct the prediction value of the FIM and prompted to confirm and correct the prediction value of the FIM, so that omission of confirmation can be avoided. As a result, the assessment value of the patient by the therapist T is appropriately recorded, and adequate rehabilitation contents for the patient can be planned.

Further, by using an actual assessment value obtained by correcting a prediction value for each item of the FIM of a patient as learning data to modify a model for calculating a prediction value, it is possible to increase the precision of calculation of the prediction value by the corrected model. In particular, by increasing the number of learning data depending on the difference between an actual assessment value and a prediction value or changing the number of learning data depending on the attribute of a therapist who has performed the assessment, it is possible to correct the model to a more adequate one.

Further, although the assessment values of items set in the FIM are used above, the values of items set in another index such that assesses the condition of a human body may be used. For example, there is an index for assessing activities of daily living such as the "Barthel Index" for assessing a total of ten items set from two viewpoints including daily living activity and locomotion activity in accordance with the degree of independence, and the values of the items of the index may be used to generate a model as described above and calculate a prediction value.

Second Example Embodiment

Figure 8:
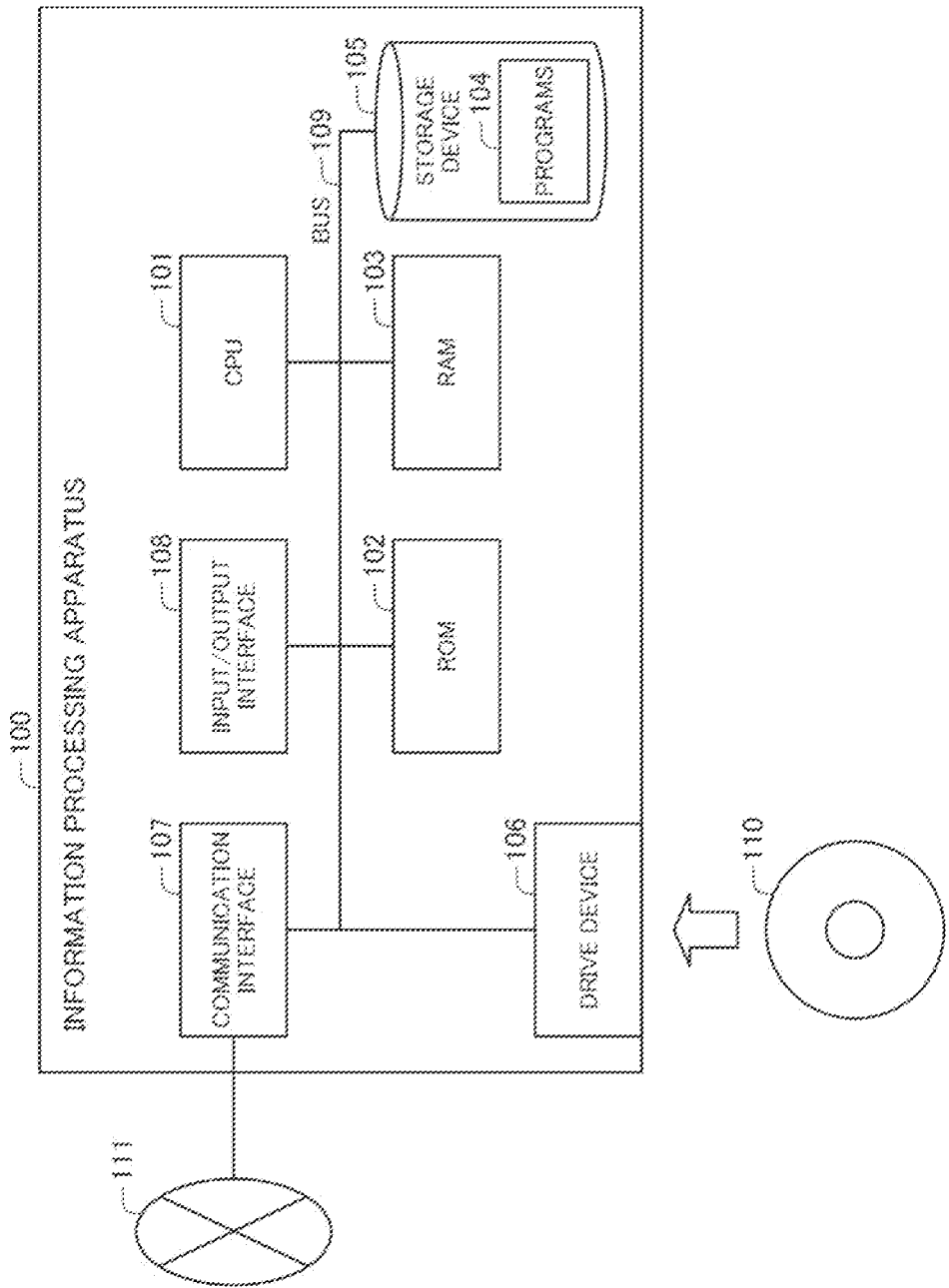
FIG. 8 is a block diagram showing a hardware configuration of an information processing apparatus in a second example embodiment of the present invention.
Figure 9:
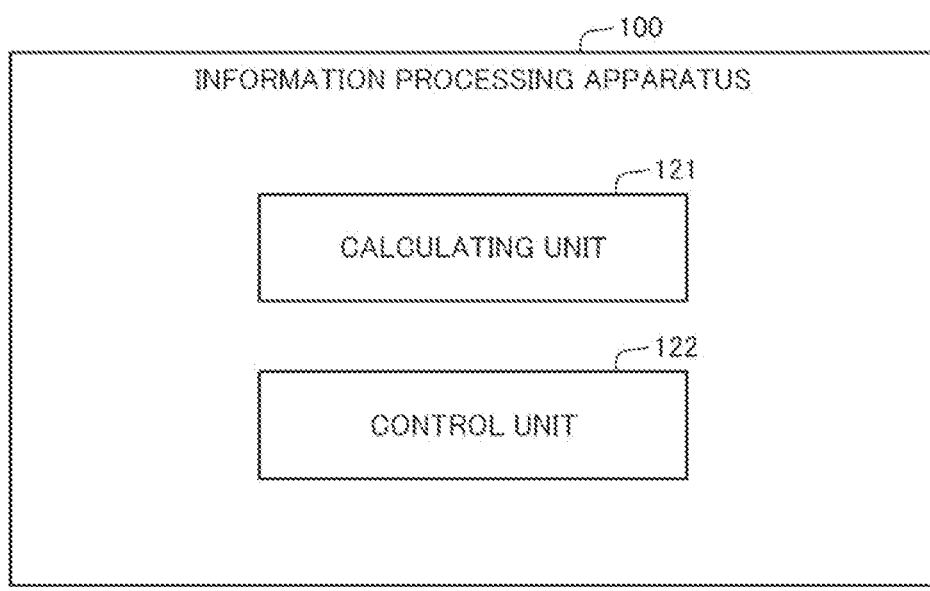
FIG. 9 is a block diagram showing a configuration of the information processing apparatus in the second example embodiment of the present invention.

Next, a second example embodiment of the present invention will be described with reference to FIGS. 8 to 10. FIGS. 8 and 9 are block diagrams showing a configuration of an information processing apparatus in the second example embodiment, and FIG. 10 is a flowchart showing an operation of the information processing apparatus. In this example embodiment, the overview of the configurations of the information processing system including the data management apparatus 10 and the information processing device 20 described in the first example embodiment and an information processing method executed by the information processing system.

First, with reference to FIG. 8, a hardware configuration of an information processing apparatus 100 in this example embodiment will be described. The information processing apparatus 100 is configured by a general information processing apparatus and includes the following hardware configuration as an example;
- a CPU (Central Processing Unit) 101 (arithmetic logic unit),
- a ROM (Read Only Memory) 102 (storage unit),
- a RAM (Random Access Memory) 103 (storage unit),
- programs 104 loaded to the RAM 103,
- a storage device 105 for storing the programs 104,
- a drive device 106 that reads from and write into a storage medium 110 outside the information processing apparatus,
- a communication interface 107 connected to a communication network 111 outside the information processing apparatus,
- an input/output interface 108 that inputs and outputs data, and
- a bus 109 that connects the respective components.

By acquisition and execution of the programs 104 by the CPU 101, the information processing apparatus 100 can structure and include a calculating unit 121 and a control unit 122 shown in FIG. 9. The programs 104 are, for example, stored in the storage device 105 or the ROM 102 in advance and loaded to the RAM 103 and executed by the CPU 101 as necessary. Moreover, the programs 104 may be supplied to the CPU 101 via the communication network 111, or may be stored in the storage medium 110 in advance to be read and supplied to the CPU 101 by the drive device 106. The abovementioned calculating unit 121 and control unit 122 may be structured by an electronic circuit.

FIG. 8 shows an example of the hardware configuration of the information processing apparatus 100, and the hardware configuration of the information processing apparatus is not limited to the abovementioned case. For example, the information processing apparatus may include part of the abovementioned configuration, for example, excluding the drive device 106.

Then, the information processing apparatus 100 executes an information processing method shown in the flowchart of FIG. 10 by the functions of the calculating unit 121 and the control unit 122 structured by the programs as described above.

As shown in FIG. 10, the information processing apparatus 100:
calculates, based on subject information including a first assessment value representing an assessment at a predetermined moment of a subject for each of a plurality of items set in FIM (Functional Independence Measure), a prediction value representing a predicted assessment after the predetermined moment of the subject (step S11); and
outputs the prediction value as a provisional assessment value representing a provisional assessment of the subject for a predetermined item of the FIM to an information processing device operated by an assessor so as to display in a correctable manner (step S12).

With the configuration as described above, the present invention calculates a prediction value representing a later assessment of a subject for each item of the FIM, and outputs the prediction value as a provisional assessment value to an information processing device operated by an assessor so as to display in a correctable manner. Since a provisional assessment value that is a prediction value is thus displayed in advance on the information processing device, it is possible to prompt an assessor to confirm and correct the provisional assessment value, and it is possible to avoid omission of confirmation. As a result, an assessment value of a subject by an assessor is recorded as necessary, and it is possible to make a plan of rehabilitation with appropriate contents for the subject.

This example embodiment is not limited to using the assessment values of the items set in the FIM, and the values of items set in another index such that assesses the condition of a human body may be used. For example, there is an index for assessing activities of daily living such as the "Barthel Index" for assessing a total of ten items set from two viewpoints including daily living activity and locomotion activity in accordance with the degree of independence, and the values of the items of the index may be used to generate a model as described above and calculate a prediction value.

<Supplementary Notes>

The whole or part of the example embodiments disclosed above can be described as the following supplementary notes. Below, the overview of the configurations of an information processing method, an information processing apparatus and a program will be described. However, the present invention is not limited to the following configurations.

(Supplementary Note 1)
An information processing method comprising:
calculating a prediction value based on subject information including a first assessment value representing an assessment of a subject at a predetermined moment for each of a plurality of items set in FIM (Functional Independence Measure), the prediction value representing an assessment of the subject predicted after the predetermined moment; and
setting the prediction value as a provisional assessment value representing a provisional assessment of the subject for a predetermined item of the FIM, and outputting so as to display in a correctable manner on an information processing device operated by an assessor.

(Supplementary Note 2)
The information processing method according to Supplementary Note 1, comprising
outputting a correction value so as to display on the information processing device, and also recording the correction value as a second assessment value representing an assessment of the subject after the predetermined moment for a predetermined item of the FIM, the correction value being obtained by correcting the provisional assessment value in accordance with an instruction from the assessor to correct the provisional assessment value output and displayed on the information processing device.

(Supplementary Note 3)
The information processing method according to Supplementary Note 2, comprising
learning so as to correct a model by using learning data including a combination of the subject information and the second assessment value, the model being for calculating the prediction value based on the subject information.

(Supplementary Note 4)
The information processing method according to Supplementary Note 3, comprising in a case where a difference between the prediction value and the correction value is equal to or more than a predetermined value, learning so as to correct the model by using the learning data including the combination of the subject information and the second assessment value.

(Supplementary Note 5)
The information processing method according to Supplementary Note 3 or 4, comprising
learning so as to correct the model by, as a difference between the prediction value and the correction value is larger, using more learning data including the combination of the subject information and the second assessment value.

(Supplementary Note 6)
The information processing method according to any of Supplementary Notes 3 to 5, comprising
in a case where the correction value is smaller than the prediction value than in a case where the correction value is larger than the prediction value, learning so as to correct the model by using more learning data including the combination of the subject information and the second assessment value.

(Supplementary Note 7)
The information processing method according to any of Supplementary Notes 3 to 6, comprising
in a case where the correction value is smaller than the prediction value than in a case where the correction value is larger than the prediction value, learning so as to correct the model in a manner that the prediction value is prevented from being predicted to be a higher value than an actual assessment value by using more learning data including the combination of the subject information and the second assessment value.

(Supplementary Note 8)
The information processing method according to any of Supplementary Notes 3 to 7, comprising
changing a number of the learning data including the combination of the subject information and the second assessment value in accordance with an attribute of the assessor having corrected the prediction value to the correction value, and learning so as to correct the model by using the learning data.

(Supplementary Note 9)
The information processing method according to any of Supplementary Notes 3 to 8, comprising
changing a number of the learning data including the combination of the subject information and the second assessment value to be more as a degree of reliability of the assessor having corrected the prediction value to the correction value is higher, and learning so as to correct the model by using the learning data.

(Supplementary Note 10)
An information processing apparatus comprising:
a calculating unit configured to calculate a prediction value based on subject information including a first assessment value representing an assessment of a subject at a predetermined moment for each of a plurality of items set in FIM (Functional Independence Measure), the prediction value representing an assessment of the subject predicted after the predetermined moment; and
a control unit configured to set the prediction value as a provisional assessment value representing a provisional assessment of the subject for a predetermined item of the FIM, and control to output so as to display in a correctable manner on an information processing device operated by an assessor.

(Supplementary Note 11)

The information processing apparatus according to Supplementary Note 10, wherein
the control unit is configured to control to output a correction value so as to display on the information processing device and also record the correction value as a second assessment value representing an assessment of the subject after the predetermined moment for a predetermined item of the FIM, the correction value being obtained by correcting the provisional assessment value in accordance with an instruction from the assessor to correct the provisional assessment value output and displayed on the information processing device.

(Supplementary Note 12)

The information processing apparatus according to Supplementary Note 11, comprising
a learning unit configured to learn so as to correct a model by using learning data including a combination of the subject information and the second assessment value, the model being for calculating the prediction value based on the subject information.

(Supplementary Note 13)

The information processing apparatus according to Supplementary Note 12, wherein
the learning unit is configured to, in a case where a difference between the prediction value and the correction value is equal to or more than a predetermined value, learn so as to correct the model by using the learning data including the combination of the subject information and the second assessment value.

(Supplementary Note 14)

The information processing apparatus according to Supplementary Note 12 or 13, wherein
the learning unit is configured to learn so as to correct the model by, as a difference between the prediction value and the correction value is larger, using more learning data including the combination of the subject information and the second assessment value.

(Supplementary Note 15)

The information processing apparatus according to any of Supplementary Notes 12 to 14, comprising
the learning unit is configured to, in a case where the correction value is smaller than the prediction value than in a case where the correction value is larger than the prediction value, learn so as to correct the model by using more learning data including the combination of the subject information and the second assessment value.

(Supplementary Note 16)

The information processing apparatus according to any of Supplementary Notes 12 to 15, wherein
the learning unit is configured to change a number of the learning data including the combination of the subject information and the second assessment value in accordance with an attribute of the assessor having corrected the prediction value to the correction value, and learn so as to correct the model by using the learning data.

(Supplementary Note 17)

A computer program comprising instructions for causing an information processing apparatus to realize:
a calculating unit configured to calculate a prediction value based on subject information including a first assessment value representing an assessment of a subject at a predetermined moment for each of a plurality of items set in FIM (Functional Independence Measure), the prediction value representing an assessment of the subject predicted after the predetermined moment; and
a control unit configured to set the prediction value as a provisional assessment value representing a provisional assessment of the subject for a predetermined item of the FIM, and control to output so as to display in a correctable manner on an information processing device operated by an assessor.

(Supplementary Note 18)

The computer program according to Supplementary Note 17, further comprising instructions for causing the information processing apparatus to realize
a learning unit configured to learn so as to correct a model by using learning data including a combination of the subject information and the second assessment value, the model being for calculating the prediction value based on the subject information.

(Supplementary Note 1.1)

An information processing method comprising:
calculating a prediction value based on subject information including a first assessment value representing an assessment of a subject at a predetermined moment for each of a plurality of items set in a predetermined index for assessing a human body condition, the prediction value representing an assessment of the subject predicted after the predetermined moment; and
setting the prediction value as a provisional assessment value representing a provisional assessment of the subject for a predetermined item of the predetermined index, and outputting so as to display in a correctable manner on an information processing device operated by an assessor.

(Supplementary Note 1.2)

The information processing method according to Supplementary Note 1, comprising
outputting a correction value so as to display on the information processing device, and also recording the correction value as a second assessment value representing an assessment of the subject after the predetermined moment for a predetermined item of the predetermined index, the correction value being obtained by correcting the provisional assessment value in accordance with an instruction from the assessor to correct the provisional assessment value output and displayed on the information processing device.

(Supplementary Note 1.3)

The information processing method according to Supplementary Note 2, comprising
learning so as to correct a model by using learning data including a combination of the subject information and the second assessment value, the model being for calculating the prediction value based on the subject information.

The abovementioned program can be stored using various types of non-transitory computer-readable mediums and supplied to a computer. The non-transitory computer-readable mediums include various types of tangible storage mediums. Examples of the non-transitory computer-readable mediums include a magnetic recording medium (for example, a flexible disk, a magnetic tape, a hard disk drive), a magnetooptical recording medium (for example, a magnetooptical disk), a CD-ROM (Read Only Memory), a CD-R, a CD-R/W, and a semiconductor memory (for example, a mask ROM, a PROM (Programmable ROM), an EPROM (Erasable PROM), a flash ROM, a RAM (Random Access Memory)). Moreover, the program may be supplied to a computer by various types of transitory computer-readable mediums. Examples of the transitory computer-readable mediums include an electric signal, an optical signal, and an electromagnetic wave. The transitory computer-readable mediums can supply the program to a computer via a wired communication path such as a wire or an optical fiber or a wireless communication path.

Although the present invention has been described with reference to the above example embodiments and so on, the present invention is not limited to the example embodiments. The configurations and details of the present invention can be changed in various manners that can be understood by one skilled in the art within the scope of the present invention.

DESCRIPTION OF NUMERALS 10 data management apparatus
11 learning unit
12 predicting unit
13 control unit
14 data storing unit
15 model storing unit
20 information processing device
T therapist
U patient
100 information processing apparatus
101 CPU
102 ROM
103 RAM
104 programs
105 storage device
106 drive device
107 communication interface
108 input/output interface
109 bus
110 storage medium
111 communication network
121 calculating unit
122 control unit

What is claimed is:

1. An information processing method comprising:
storing a model for obtaining prediction values of assessment in rehabilitation for a subject;
calculating, using the model, by one or more processors, a prediction value based on subject information including a first assessment value representing an assessment of the subject at a predetermined moment for each of a plurality of items set in FIM (Functional Independence Measure), the prediction value representing an assessment of the subject predicted after the predetermined moment;
setting, by the one or more processors, the prediction value as a provisional assessment value representing a provisional assessment of the subject for a predetermined item of the FIM;
outputting a display control signal for controlling display, on a display device, of the prediction value in a correctable manner on an information processing device operated by an assessor for the assessor to consider in decision-making regarding whether to modify the prediction value;
in a case where an input from the assessor is received via the information processing device,
obtaining, by the one or more processors, a correction value based on an input from the assessor provided via the information processing device, the correction value representing an assessment of the subject for the plurality of items;
recording, by the one or more processors, the correction value as a second assessment value representing an assessment of the subject for a predetermined item of the FIM; and
in a case where a difference between the prediction value and the correction value is equal to or more than a predetermined value, by the one or more processors, changing a number of learning data including a combination of the subject information and the second assessment value in accordance with an attribute of the assessor, and performing machine learning to correct the model by using the learning data to increase precision of calculating the prediction value; and
in a case where no input is received from the assessor via the information processing device,
by the one or more processors, performing either one of: notifying an alert to a supervisor of the assessor via the display device or notifying an alert to the assessor via the display device before starting the rehabilitation of the subject after the predetermined moment.

2. The information processing method according to claim 1, comprising
learning, by the one or more processors, to correct the model by, as the difference between the prediction value and the correction value increases, increasing the number of learning data.

3. The information processing method according to claim 1, comprising
in a case where the correction value is smaller than the prediction value, increasing, by the one or more processors, the learning data $\alpha$ times; and
in a case where the correction value is larger than the prediction value, increasing, by the one or more processors, the learning data $\gamma*\alpha$ times,
wherein $\alpha$ and $\gamma$ are positive values larger than 1.

4. The information processing method according to claim 1, comprising
in a case where the correction value is smaller than the prediction value, learning, by the one or more processors, so as to correct the model in a manner that the prediction value is prevented from being higher than an actual assessment value by increasing the number of learning data.

5. The information processing method according to claim 1,
wherein the attribute of the assessor corresponds to a degree of reliability of the assessor.

6. An information processing apparatus comprising:
at least one memory configured to store instructions; and
at least one processor configured to execute the instructions to:
store a model for obtaining prediction values of assessment in rehabilitation for a subject;
calculate, using the model, a prediction value based on subject information including a first assessment value representing an assessment of the subject at a predetermined moment for each of a plurality of items set in FIM (Functional Independence Measure), the prediction value representing an assessment of the subject predicted after the predetermined moment;

set the prediction value as a provisional assessment value representing a provisional assessment of the subject for a predetermined item of the FIM;

control to output a display control signal to control display of the prediction value in a correctable manner on a display device of an information processing device operated by an assessor for the assessor to consider in decision-making regarding whether to modify the prediction value;

in a case where an input from the assessor is received via the information processing device,
- obtain a correction value based on an input from the assessor provided via the information processing device, the correction value representing an assessment of the subject for the plurality of items;
- record the correction value as a second assessment value representing an assessment of the subject for a predetermined item of the FIM; and
- in a case where a difference between the prediction value and the correction value is equal to or more than a predetermined value, change a number of learning data including a combination of the subject information and the second assessment value in accordance with an attribute of the assessor, and perform machine learning to correct the model by using the learning data to increase precision of calculating the prediction value; and in a case where no input is received from the assessor via the information processing device,
- perform either one of: notifying an alert to a supervisor of the assessor via the display device or notifying an alert to the assessor via the display device before starting the rehabilitation of the subject after the predetermined moment.

7. The information processing apparatus according to claim 6, wherein the at least one processor is configured to execute the instructions to
learn to correct the model by, as the difference between the prediction value and the correction value increases, increase the number of learning data.

8. The information processing apparatus according to claim 6, wherein the at least one processor is configured to execute the instructions to,
in a case where the correction value is smaller than the prediction value, increase the learning data $\alpha$ times; and
in a case where the correction value is larger than the prediction value, increase the learning data $\gamma*\alpha$ times, wherein $\alpha$ and $\gamma$ are positive values larger than 1.

9. A non-transitory computer-readable storage medium having a program stored therein, the program comprising instructions for causing an information processing apparatus to execute:
- a process to store a model for obtaining prediction values of assessment in rehabilitation for a subject;
- a process to calculate, using the model, a prediction value based on subject information including a first assessment value representing an assessment of the subject at a predetermined moment for each of a plurality of items set in FIM (Functional Independence Measure), the prediction value representing an assessment of the subject predicted after the predetermined moment;
- a process to set the prediction value as a provisional assessment value representing a provisional assessment of the subject for a predetermined item of the FIM;
- a process to control to output a display control signal to control display of the prediction value in a correctable manner on a display device of an information processing device operated by an assessor for the assessor to consider in decision-making regarding whether to modify the prediction value;

in a case where an input from the assessor is received via the information processing device,
- a process to obtain a correction value based on an input from the assessor provided via the information processing device, the correction value representing an assessment of the subject for the plurality of items;
- a process to record the correction value as a second assessment value representing an assessment of the subject for a predetermined item of the FIM; and
- a process to, in a case where a difference between the prediction value and the correction value is equal to or more than a predetermined value, change a number of learning data including a combination of the subject information and the second assessment value in accordance with an attribute of the assessor, and perform machine learning to correct the model by using the learning data to increase precision of calculating the prediction value; and in a case where no input is received from the assessor via the information processing device,
- a process to perform either one of: notifying an alert to a supervisor of the assessor via the display device or notifying an alert to the assessor via the display device before starting the rehabilitation of the subject after the predetermined moment.

* * * * *